(12) United States Patent
Toraya

(10) Patent No.: US 7,801,272 B2
(45) Date of Patent: Sep. 21, 2010

(54) X-RAY DIFFRACTION APPARATUS AND X-RAY DIFFRACTION METHOD

(75) Inventor: Hideo Toraya, Tachikawa (JP)

(73) Assignee: Rigaku Corporation, Akishima-shi (JP)

(*) Notice: Subject to any disclaimer, the term of this patent is extended or adjusted under 35 U.S.C. 154(b) by 76 days.

(21) Appl. No.: 12/190,790

(22) Filed: Aug. 13, 2008

(65) Prior Publication Data

US 2009/0086921 A1    Apr. 2, 2009

(30) Foreign Application Priority Data

Sep. 28, 2007  (JP) .............................. 2007-253394
Sep. 28, 2007  (JP) .............................. 2007-253425

(51) Int. Cl.
*G01N 23/20*   (2006.01)
*G21K 1/06*    (2006.01)

(52) U.S. Cl. .............................. 378/71; 378/73; 378/84; 378/85

(58) Field of Classification Search .................. 378/71, 378/73, 75, 76, 84, 85
See application file for complete search history.

(56) References Cited

U.S. PATENT DOCUMENTS

| | | | | |
|---|---|---|---|---|
| 4,351,063 A | * | 9/1982 | Dineen et al. .................. | 378/79 |
| 4,949,367 A | * | 8/1990 | Huizing et al. ................ | 378/84 |
| 5,406,609 A | * | 4/1995 | Arai et al. ..................... | 378/73 |
| 5,923,720 A | * | 7/1999 | Barton et al. ................. | 378/84 |
| 6,069,934 A | * | 5/2000 | Verman et al. ................ | 378/73 |
| 6,226,349 B1 | * | 5/2001 | Schuster et al. .............. | 378/84 |
| 6,459,763 B1 | * | 10/2002 | Koinuma et al. .............. | 378/71 |
| 6,731,719 B2 | * | 5/2004 | Fewster et al. ................ | 378/71 |

(Continued)

FOREIGN PATENT DOCUMENTS

JP      06-082398 A      3/1994

(Continued)

OTHER PUBLICATIONS

H. Toraya et al; A New Powder Diffractometer for Synchrotron Radiation With a Multiple-Detector System; 1996; Journal of Synchrotron Radiation; pp. 75-83.

(Continued)

*Primary Examiner*—Allen C. Ho
(74) *Attorney, Agent, or Firm*—Frishauf, Holtz, Goodman & Chick, P.C.

(57) ABSTRACT

In an X-ray diffraction method using the parallel beam method, an X-ray parallel beam is incident on a sample, and diffracted X-rays from the sample are reflected at a mirror and thereafter detected by an X-ray detector. The reflective surface of the mirror has a shape of an equiangular spiral that has a center located on the surface of the sample. A crystal lattice plane that causes reflection is parallel to the reflective surface at any point on the reflective surface. The X-ray detector is one-dimensional position sensitive in a plane parallel to the diffraction plane. A relative positional relationship between the mirror and the X-ray detector is determined so that reflected X-rays from different points on the reflective surface of the mirror reach different points on the X-ray detector respectively. This X-ray diffraction method is superior in angular resolution, and is small in X-ray intensity reduction, and is simple in structure.

13 Claims, 14 Drawing Sheets

U.S. PATENT DOCUMENTS

| | | | |
|---|---|---|---|
| 6,807,251 B2 * | 10/2004 | Okanda et al. | 378/71 |
| 6,873,681 B2 * | 3/2005 | Toraya et al. | 378/71 |
| 6,934,359 B2 * | 8/2005 | Chen et al. | 378/84 |
| 7,145,983 B2 * | 12/2006 | Taguchi et al. | 378/71 |
| 7,443,952 B2 * | 10/2008 | Dosho et al. | 378/71 |
| 7,471,766 B2 * | 12/2008 | Dosho | 378/71 |
| 7,535,992 B2 * | 5/2009 | Taguchi et al. | 378/124 |

FOREIGN PATENT DOCUMENTS

| | | |
|---|---|---|
| JP | 07-063897 A | 3/1995 |
| JP | 07-072298 A | 3/1995 |

OTHER PUBLICATIONS

The High Resolution Powder Diffraction Beam Line at ESRF; Jan.-Feb. 2004; Journal of Research of the National Institute of Standards and Technology; pp. 133-142.

\* cited by examiner $$y_{DB} = \tan\phi \cdot x \quad (1)$$

$$\frac{dy}{dx} = -\tan(\theta_0 - \phi) \quad (2)$$

$$\frac{y}{x} = \tan\phi \quad (3)$$

$$a = \tan\theta_0 \quad (4)$$

$$\frac{dy}{dx} = \frac{\frac{y}{x} - a}{1 + a\frac{y}{x}} \quad (5)$$

$$\ln\left[\frac{x}{r}\left(1 + \frac{y^2}{x^2}\right)^{1/2}\right] = -\frac{1}{a}\tan^{-1}\frac{y}{x} \quad (6)$$

$$\ln\left[\frac{x}{r}(1 + \tan^2\phi)^{1/2}\right] = -\frac{\phi}{\tan\theta_0} \quad (7)$$

In a range of $-\pi/2 \leqq \phi \leqq \pi/2$ $$(1+\tan^2 \phi)^{-1/2} = \cos \phi \qquad (8)$$

$$x = r \cdot \exp\left(-\frac{\phi}{\tan \theta_0}\right) \cos \phi \qquad (9)$$

$$y = r \cdot \exp\left(-\frac{\phi}{\tan \theta_0}\right) \sin \phi \qquad (10)$$

$$y_{\tan} = -\tan \theta_0 \, (x-200) \qquad (11)$$

$$A = r \cdot \exp\left(-\frac{\phi}{\tan\theta_0}\right) \qquad (12)$$

$$y = -\tan(2\theta_0 - \phi)(x - A\cos\phi) + A\sin\phi \qquad (13)$$

$$y = -\tan 2\theta_0 (x - r) \qquad (14)$$

$$x_p = r\frac{\sin 4\theta_0}{2}\left[\frac{1}{\tan\phi} + \tan 2\theta_0 - \exp\left(-\frac{\phi}{\tan\theta_0}\right)\frac{1}{\sin\phi}\right] \qquad (15)$$

FIG. 6

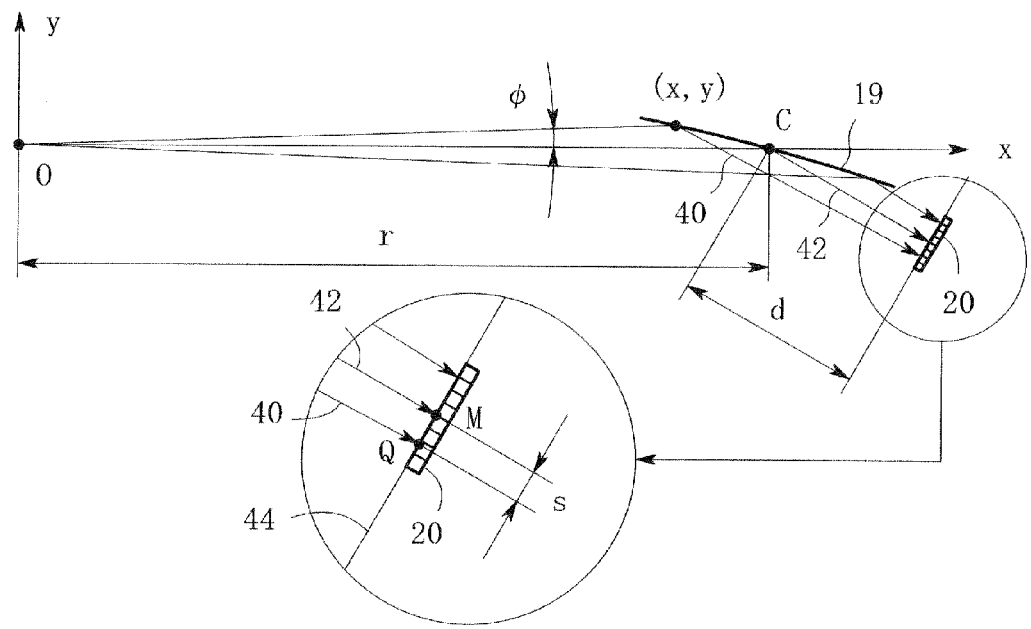

$$(x_m, y_m) = (r+d\cos2\theta_0, -d\sin2\theta_0) \tag{16}$$

$$y = \frac{1}{\tan2\theta_0}[x-(r+d\cos2\theta_0)]-d\sin2\theta_0 \tag{17}$$

$$x_q = \sin2\theta_0\left[\tan\phi\,(d+r\cos2\theta_0)+\sin2\theta_0\left(\frac{A}{\cos\phi}-r\right)\right]+r+d\cos2\theta_0 \tag{18}$$

$$y_q = \cos2\theta_0\left[\tan\phi\,(d+r\cos2\theta_0)+\sin2\theta_0\left(\frac{A}{\cos\phi}-r\right)\right]-d\sin2\theta_0 \tag{19}$$

$$s = \left|\tan\phi\,(d+r\cos2\theta_0)+\sin2\theta_0\left[\exp\left(-\frac{\phi}{\tan\theta_0}\right)\frac{1}{\cos\phi}-1\right]r\right| \tag{20}$$

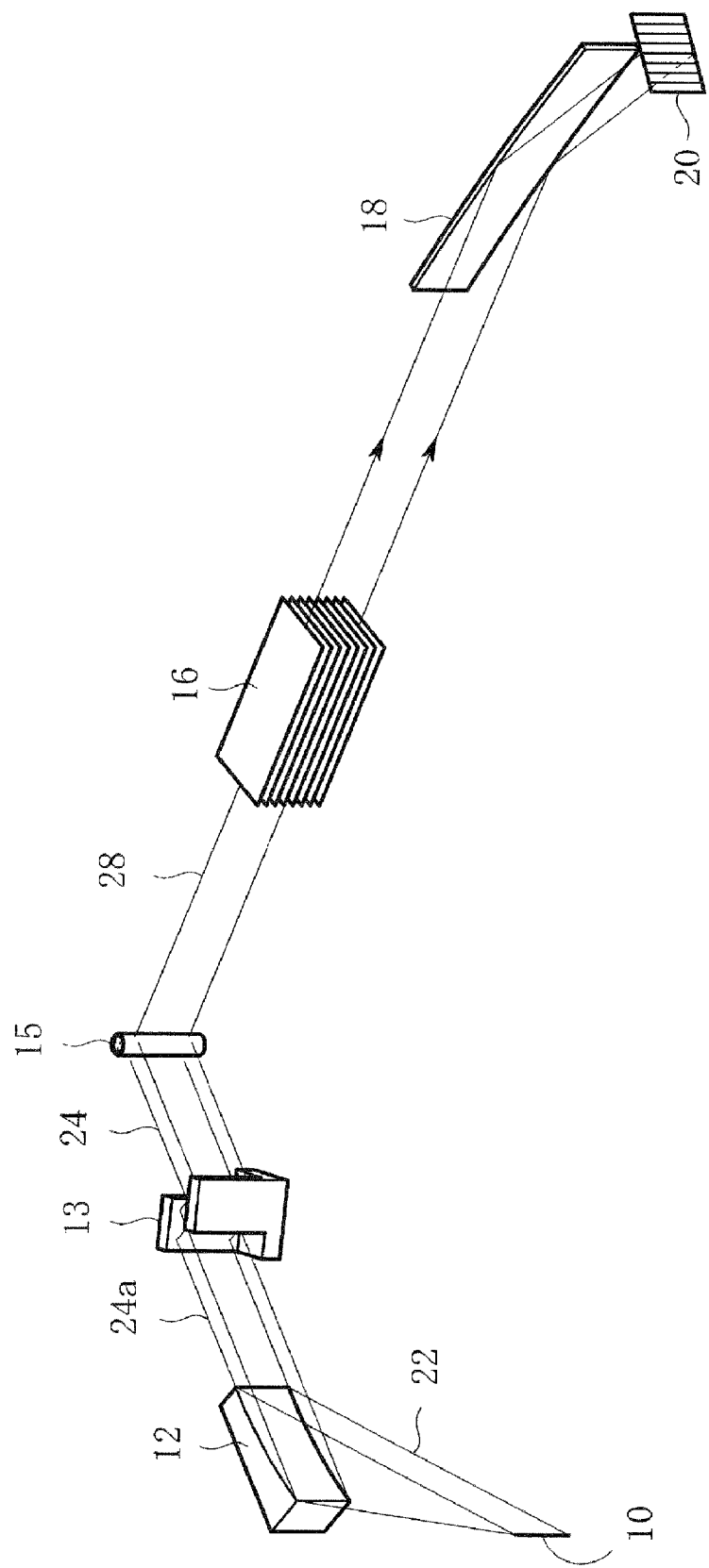

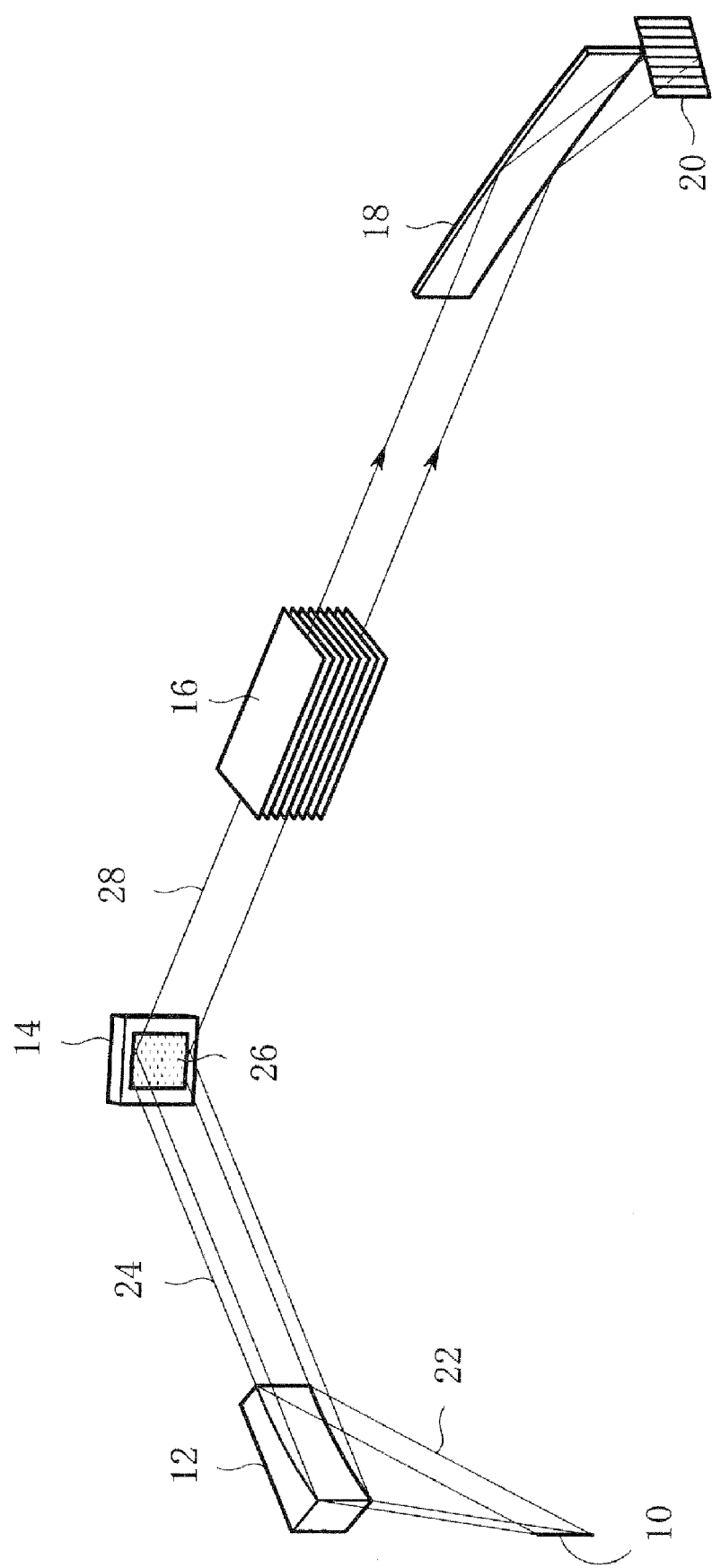

$$y = A_i \tan\phi_i \cdot x \qquad (21)$$

$$A_i = r \cdot \exp\left(-\frac{\phi_i}{\tan\theta_0}\right) \qquad (22)$$

X-RAY DIFFRACTION APPARATUS AND X-RAY DIFFRACTION METHOD

BACKGROUND OF THE INVENTION

The present invention relates to an X-ray diffraction apparatus and an X-ray diffraction method with the use of the parallel beam method.

In the powder X-ray diffraction method for powder samples, thin film samples or polycrystalline samples, an analyzer must be inserted into a diffracted-beam-side optical system (i.e., a receiving optical system) in order to improve the angular resolution when using the parallel beam method. One of known analyzers is a long parallel slit having a narrow angle of X-ray aperture, and the other is an analyzer crystal. The method with the long parallel slit is not so severe in X-ray intensity reduction but is inferior in angular resolution. On the contrary, the method with the analyzer crystal is superior in angular resolution but is severe in X-ray intensity reduction. Therefore, in the parallel beam method, there is desired a suitable analyzer that is superior in angular resolution and is small in X-ray intensity reduction.

An improvement in using the analyzer crystal and preventing the radiation intensity reduction in totality is known as disclosed in Journal of Synchrotron Radiation (1996), 3, 75-83 (which will be referred to as the first publication hereinafter) and Journal of Research of the National Institute of Standards and Technology, 109, 133-142 (2004) (which will be referred to as the second publication hereinafter).

The first publication discloses that plural (for example, six) X-ray detectors (which are scintillation counters) are located around a sample in the powder diffraction method using synchrotron orbit radiation. An analyzer crystal made of a Ge(111) flat plate is inserted between the sample and each of the X-ray detectors. The use of the plural X-ray detectors enables a short-time measurement of a diffraction pattern with a predetermined angular range as compared to the case using a single X-ray detector. Accordingly, the X-ray intensity reduction caused by the use of the analyzer crystals is prevented in totality of the apparatus.

The second publication discloses that, as well as the first publication, plural (for example, nine) analyzer crystals and as many X-ray detectors (scintillation counters) are located around a sample in the powder diffraction method.

By the way, the present invention is concerned with the use of a mirror having a reflective surface shaped in an equiangular spiral (a logarithmic spiral) in an X-ray diffraction apparatus with the parallel beam method. On the other hand, as to an X-ray diffraction apparatus with the focusing beam method, the use of a mirror (analyzing crystal) having an equiangular spiral reflective surface is disclosed in Japanese Patent Publication No. 6-82398 A (1994) (which will be referred to as the third publication hereinafter), Japanese Patent Publication No. 7-63897 A (1995) (which will be referred to as the fourth publication hereinafter), and Japanese Patent Publication No. 7-72298 A (1995) (which will be referred to as the fifth publication hereinafter).

The third publication discloses an analyzer crystal, which has a reflective surface shaped in a logarithmic spiral. The analyzer crystal is made of a synthetic multilayer lattice, in which the farther a point on the reflective surface is away from the X-ray source, the larger the lattice spacing is. The fourth publication discloses an X-ray spectrometer according to the second embodiment, which is composed of a combination of plural flat elements. Each flat element has a reflective point located on a curve that is nearly a logarithmic spiral. Each flat element is made of a synthetic multilayer lattice, in which the farther a point on the reflective surface is away from the X-ray source, the larger the lattice spacing is. The fifth publication discloses an X-ray spectroscopic element according to the fourth embodiment, which is composed of a combination of curved reflective surfaces with steps therebetween, each reflective surface having a longitudinal cross section close to a logarithmic spiral curve. Each reflective surface is made of a synthetic multilayer lattice, in which the farther the reflective surface is away from the X-ray source, the larger the lattice spacing is.

The structure that places plural analyzer crystals and plural X-ray detectors around a sample as disclosed in the first and second publications is so complex and expensive that it is hardly applicable to an X-ray diffraction method in a laboratory system.

The mirror having a reflective surface with a variable lattice spacing as disclosed in the third, fourth and fifth publications can not be used as a mirror, in the parallel beam method, for reflecting an X-ray beam having a different incident angle toward a different place.

SUMMARY OF THE INVENTION

It is an object of the present invention to provide an X-ray diffraction apparatus and method, which is superior in angular resolution, small in X-ray intensity reduction, and simple in structure as compared to the prior art using plural analyzer crystals and as many X-ray detectors.

It is another object of the present invention to provide an X-ray diffraction apparatus and method, which can restrain X-ray intensity reduction with remaining good angular resolution even when the width of an incident X-ray beam is comparatively large.

In an X-ray diffraction apparatus according to the first type of the present invention, an X-ray parallel beam is incident on a sample, and diffracted X-rays from the sample are reflected at a mirror using diffraction phenomena and thereafter detected by an X-ray detector. The mirror has a reflective surface, which is formed so that an angle, in a plane parallel to a diffraction plane, between a tangential line of the reflective surface at any point on the reflective surface and a line segment connecting the any point and the sample becomes constant, and a crystal lattice plane that causes reflection is parallel to the reflective surface at any point on the reflective surface. The X-ray detector is one-dimensional position sensitive in a plane parallel to the diffraction plane. A relative positional relationship between the mirror and the X-ray detector is determined, in a plane parallel to the diffraction plane, so that reflected X-rays from different points on the reflective surface of the mirror reach different points on the X-ray detector respectively. In the present invention, the cross sectional shape (the shape in a plane parallel to the diffraction plane) of the reflective surface of the mirror becomes a continuously curved line, the curved reflective surface is suitable for the case that the beam width (the beam width in the diffraction plane) of the parallel beam is small.

The reflective surface of the mirror may preferably be shaped in an equiangular spiral (which is also called a logarithmic spiral) in a plane parallel to the diffraction plane, a center of the equiangular spiral being located on a surface of the sample.

In an X-ray diffraction method according to the first type of the present invention, as well as the above-described X-ray diffraction apparatus according the first type invention, an X-ray parallel beam is incident on a sample, and diffracted X-rays from the sample are reflected at a mirror using diffraction phenomena and thereafter detected by an X-ray detector.

The feature regarding the reflective surface of the mirror, the feature regarding the X-ray detector, and the feature regarding the relative positional relationship between the mirror and the X-ray detector are the same as those in the above-described X-ray diffraction apparatus according to the first type invention. In addition, different diffracted X-rays having different diffraction angles are reflected at the mirror and thereafter detected distinctly and simultaneously by the X-ray detector.

In an X-ray diffraction apparatus according to the second type of the present invention, an X-ray parallel beam is incident on a sample, and diffracted X-rays from the sample are reflected at a mirror using diffraction phenomena and thereafter detected by an X-ray detector. The mirror has a reflective surface consisting of a combination of plural flat reflective surfaces, which are located so that an angle, in a plane parallel to a diffraction plane, between each flat reflective surface and a line segment connecting a center of the each flat reflective surface and the sample becomes constant among all the flat reflective surfaces, and a crystal lattice plane that causes reflection in each flat reflective surface is parallel to the each flat reflective surface. The X-ray detector is one-dimensional position sensitive in a plane parallel to the diffraction plane. A relative positional relationship between the flat reflective surfaces and the X-ray detector is determined, in a plane parallel to the diffraction plane, so that reflected X-rays that have been reflected at different flat reflective surfaces reach different points on the X-ray detector respectively.

Respective centers of the flat reflective surfaces may preferably be located, in a plane parallel to the diffraction plane, on an equiangular spiral having a center that is located on a surface of the sample.

In an X-ray diffraction method according to the second type of the present invention, as well as the above-described X-ray diffraction apparatus according the second type invention, an X-ray parallel beam is incident on a sample, and diffracted X-rays from the sample are reflected at a mirror using diffraction phenomena and thereafter detected by an X-ray detector. The feature regarding the reflective surface of the mirror, the feature regarding the X-ray detector, and the feature regarding the relative positional relationship between the mirror and the X-ray detector are the same as those in the above-described X-ray diffraction apparatus according to the second type invention. In addition, different diffracted X-rays having different diffraction angles are reflected at the mirror and thereafter detected distinctly and simultaneously by the X-ray detector.

The first and second types of the present invention have an advantage that a combination of an analyzer crystal having a reflective surface with the predetermined shape and a single, one-dimensional position sensitive X-ray detector brings a superior angular resolution, less reduction of an X-ray intensity, and a simple structure as compared to the prior art using plural analyzer crystals.

In addition, the second type of the present invention has an advantage that even when the width of an X-ray beam that is incident on a sample is comparatively large, the use of the mirror having a shape based on a new mathematical equation brings prevention of angular resolution reduction caused by X-ray optical aberration and prevention of X-ray intensity reduction, so that both a superior angular resolution and a superior X-ray intensity gain are attained.

BRIEF DESCRIPTION OF THE DRAWINGS

FIG. 6 shows an explanatory illustration indicating a positional relationship between the mirror and an X-ray detector and shows concerned mathematical equations;

FIG. 7 is a schematic perspective view of a modified optical system of the X-ray diffraction apparatus shown in FIG. 1;

FIG. 8 is a schematic perspective view of another modified optical system of the X-ray diffraction apparatus shown in FIG. 1;

DETAILED DESCRIPTION OF THE PREFERRED EMBODIMENTS

Figure 1:
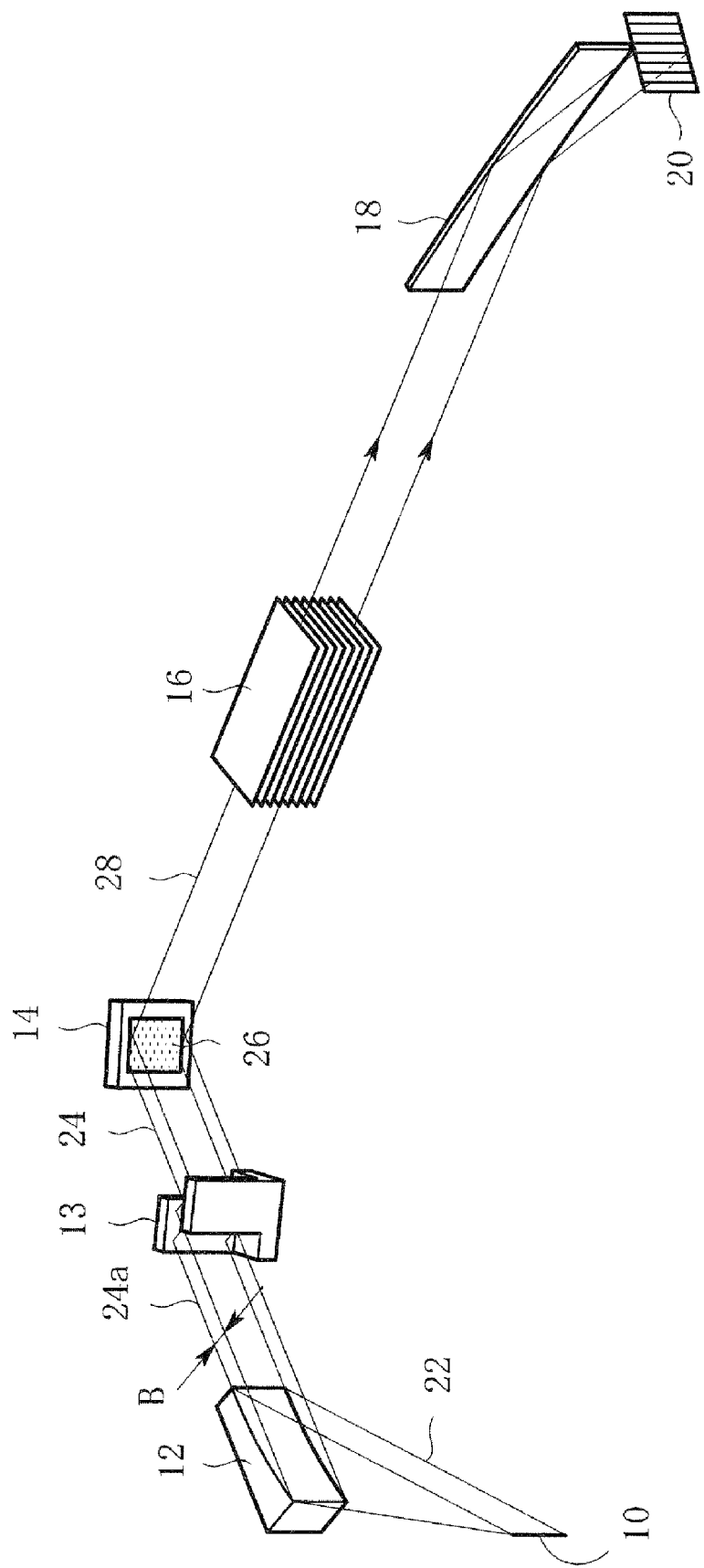
FIG. 1 is a schematic perspective view of an X-ray diffraction apparatus according to the first type of the present invention.

Embodiments of the present invention will now be described in detail below with reference to the drawings. FIG. 1 is a schematic perspective view of the X-ray diffraction apparatus according to the first type of the present invention. The X-ray diffraction apparatus comprises an X-ray source having a linear (or point-like) X-ray focus 10, a multilayer mirror 12 having a parabolic-shaped reflective surface, a channel cut monochromator 13 for selecting a characteristic X-ray Kα1, a sample holder 14, a Soller slit 16 for restricting vertical divergence of diffracted X-rays, a mirror 18 made of an analyzer crystal, and a one-dimensional position sensitive X-ray detector 20. FIG. 1 shows the case using a linear X-ray focus. A divergent beam 22, which consists of X-rays emitted from the X-ray focus 10, is converted into a parallel beam 24a by the multilayer mirror 12 having a parabolic reflective surface. The multilayer mirror 12 is optimized for the X-ray wavelength to be used (CuKα1 in this embodiment) and has a gradient lattice spacing. The X-ray focus 10 is placed at a parabolic-focus position of the multilayer mirror 12. Assuming the use of a linear X-ray focus for example, the X-ray focus 10 is about ten millimeters long in the vertical direction. The parallel beam 24a passes through the channel cut monochromator 13 and the resultant parallel beam 24 (an incident X-ray) is incident on a sample 26. A beam width B of the parallel beam 24a and the parallel beam 24 in the horizontal plane is approximately 0.84 millimeter. The sample 26 is powdery and the recess of the sample holder 14 is filled with the sample 26. Diffracted X-rays 28 will come from the sample 26. The diffracted X-rays 28 are restricted in vertical divergence by the Soller slit 16.

The sample 26 is not limited to powder, but a polycrystalline substance (metal and so on), a thin film sample on a substrate, and a filament sample may be used. Any sample holder for so-called reflection-type X-ray diffraction analysis may be used. In addition, a sample holder for transmission-type X-ray diffraction analysis may be used: for example, as shown in FIG. 7, a capillary tube 15 may be filled with a sample.

FIG. 8 shows a modified optical system of the X-ray diffraction apparatus shown in FIG. 1. The modified embodiment differs from the apparatus shown in FIG. 1 in that the channel cut monochromator is omitted in the incident-side optical systems and the multilayer mirror 12 is optimized for the X-ray wavelength to be used in this embodiment (CuKα in this embodiment, i.e., the doublet of CuKα1 and CuKα2).

Referring back to FIG. 1, a plane including both the incident X-ray 24 and the diffracted X-ray 28 is generally called a diffraction plane or a equatorial plane. In this specification, the plane including both the incident X-ray 24 and the diffracted X-ray 28 is defined as the diffraction plane. An X-ray divergence in the diffraction plane is generally called an equatorial divergence or a radial divergence. In this specification, the divergence in the diffraction plane is called a horizontal divergence, whereas a divergence in a plane perpendicular to the diffraction plane is called a vertical divergence. In the optical system shown in FIG. 1, the diffraction plane exists in the horizontal plane, and the X-ray focus 10 stands upright, and the surface of the sample 26 also stands upright.

The Soller slit 16 restricts the vertical divergence. The horizontal divergence in the parallel beam method, which affects directly a resolution of the detected diffraction angle, is severely restricted by both the mirror 18 that will be described later and the channel cut monochromator 13 described above. The mirror 18 is a key component in the present invention, which guarantees a superior angular resolution of the diffracted X-ray 28: this feature will be explained in detail later. An approximate size of the mirror 18 is in a range between 15 and 20 millimeters in height and in a range between 60 and 80 millimeters in length. The mirror 18 is slightly curved away from a flat plane. The channel cut monochromator 13 uses a Ge(220) lattice plane when the X-ray target to be used is Cu.

The one-dimensional position sensitive X-ray detector 20 uses a silicon strip detector (SSD) in this embodiment. The detector is one-dimensional position sensitive in a plane parallel to the diffraction plane. That is to say, one upright elongated detector plane forms one detector channel, and many channels (for example, 128 channels) are arranged side by side in the horizontal direction. A size of one channel is, for example, 0.1 millimeter in width and 15 millimeters in length (height in FIG. 1).

Figure 2:
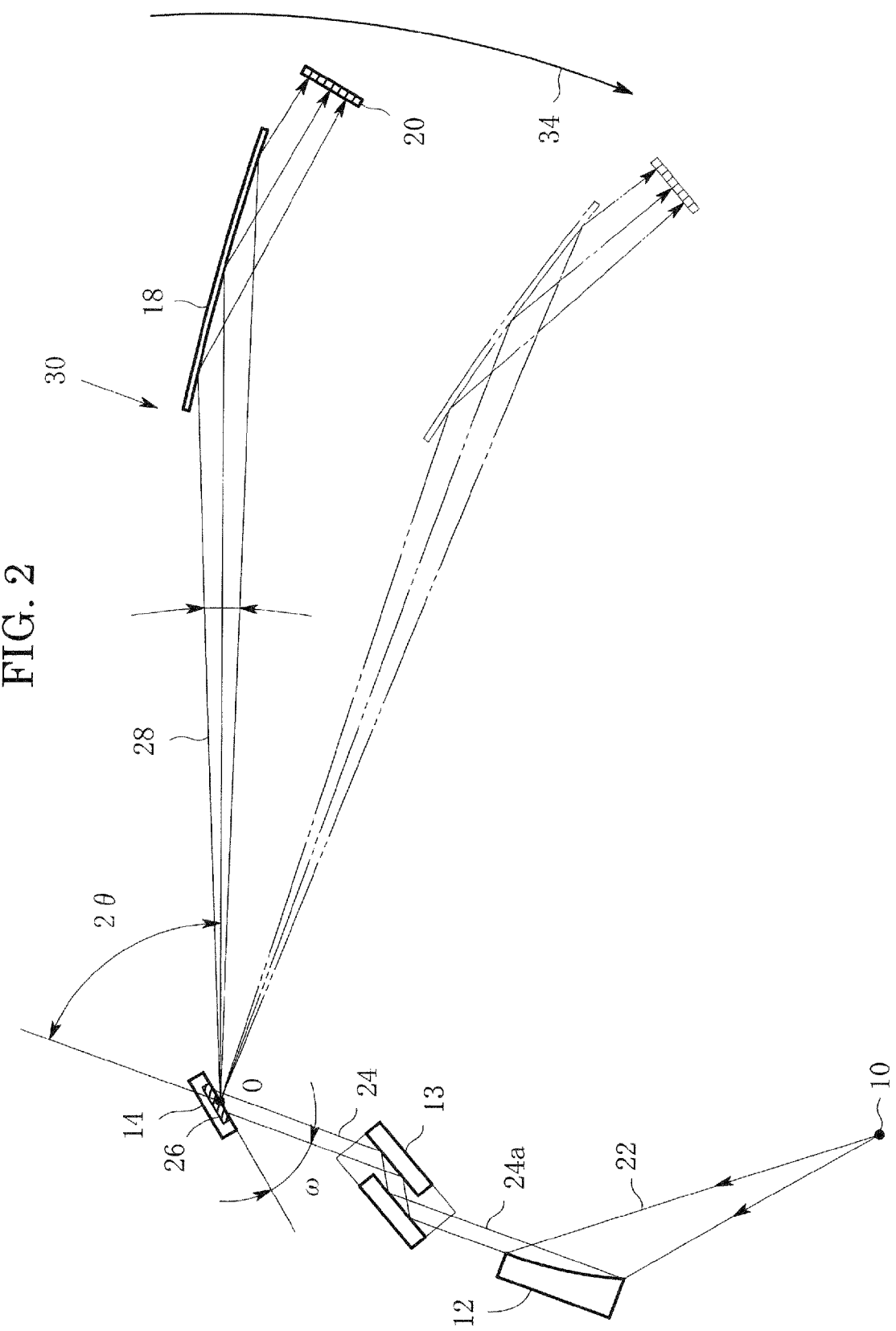
FIG. 2 is a plan view of the X-ray diffraction apparatus shown in FIG. 1.

FIG. 2 is a plan view of the X-ray diffraction apparatus shown in FIG. 1. An angle between the incident X-ray 24 and the diffracted X-ray 28 is 2θ. The angle θ is the Bragg angle of X-ray diffraction for the sample 26. When measuring a diffraction pattern with a predetermined angular range with the use of this X-ray diffraction apparatus, the sample holder 14 and a receiving optical system 30 rotate synchronously to keep a relationship between an angle ω of an incident X-ray 24 to a surface of the sample 26 and the angle 2θ described above into a ratio of 1 to 2. An X-ray diffraction pattern coming from the sample 26 is thus detected. The receiving optical system 30 consists mainly of the Soller slit 16 (see FIG. 1, it is omitted in FIG. 2), the mirror 18, and the X-ray detector 20, these optical components being mounted in a receiving arm (not shown). The receiving optical system 30 is, as indicated by an arrow 34, rotatable around the center of goniometer (point O). The surface of the sample 26 is located on the center of goniometer (point O).

Since the X-ray diffraction apparatus uses the parallel beam method, there is usable another measurement method that does not keep the relationship between ω and 2θ into the ratio of 1 to 2. Namely, when a diffraction pattern is measured with a predetermined angular range, the sample holder 14 may be kept stationary to keep the angle ω of the incident X-ray 24 to the surface of the sample 26 constant. Although the diffracted X-rays 28 from the sample 26 travel in different directions depending on the Bragg angles, those diffracted X-rays 28 can be detected with the use of the rotation of the receiving optical system 30.

Next, the shape of the reflective surface of the mirror 18 will be described in detail below. The mirror 18 is formed by slightly bending a single crystal thin plate. In this embodiment, the mirror 18 is made of a single crystal of Ge, and it is formed so that Ge(111) plane is parallel to the surface of the mirror. The mirror is to reflect, with the diffraction phenomena, the diffracted X-ray coming from the sample. The Ge(111) plane corresponds to the crystal lattice plane that causes diffraction.

Figure 3:
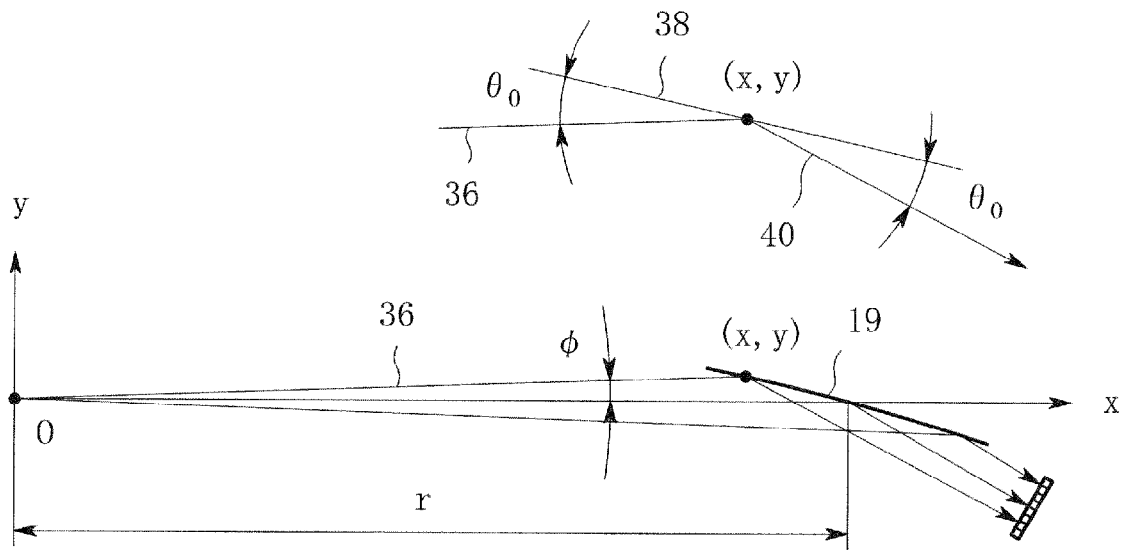
FIG. 3 shows an explanatory illustration for explaining how to obtain a shape of a reflective surface of a mirror and shows concerned mathematical equations.

Referring to FIG. 3, the reflective surface 19 of the mirror has a shape of an equiangular spiral (which is also called a logarithmic spiral) in a plane parallel to the diffraction plane. FIG. 3 shows a view in a plane parallel to the diffraction plane. The feature of the equiangular spiral is that an angle $\theta_0$ between a tangential line 38 at any point (x, y) on the equiangular spiral and a line segment 36 that connects the any point (x, y) and the center of spiral (point O) is constant in any point on the spiral. It is the reason why the spiral is called "equiangular" spiral. The angle $\theta_0$ is set to be equal to the Bragg angle of Ge(111) for the X-ray wavelength to be used. In this embodiment, the mirror is made for CuKα1, and thus the angle $\theta_0$ is 13.64 degrees. The diffracted X-ray (that has been diffracted by the sample) that goes from the point O to the reflective surface is to be incident on the reflective surface 19 with an incidence angle $\theta_0$ to the tangential line 38 of the reflective surface 19 at any incident point on the reflective surface, so that the diffracted X-ray always satisfies the Bragg's condition. A reflected X-ray 40 that has reflected at the reflective surface 19 goes out with the angle $\theta_0$ to the tangential line 38 similarly.

The shape of the reflective surface 19 of the mirror can be determined as described below. Referring to FIG. 3, the center of goniometer (point O) is defined as the origin of the x-y coordinate system. The surface of the sample is located on the point O, and the center of the equiangular spiral is also located on the point O. It is assumed that the central region of the reflective surface 19 is located at a point of x=r on the x-axis. When a diffracted X-ray 36 travels in a direction at an angle φ (toward the counterclockwise direction) to the X-axis, the diffracted X-ray 36 reaches the point (x, y) on the reflective surface 19. The diffracted X-ray 36 may be expressed by an equation (1) in FIG. 3, the coordinates (x, y) of each point on the diffracted X-ray track satisfying equation (1). Namely, y-coordinate of the diffracted X-ray, i.e., $y_{DB}$, is expressed with the angle $\phi$ and x-coordinate.

A slope dy/dx of the reflective surface 19 at the point (x, y) is expressed by equation (2). Equation (2) may be transformed into equation (5) with the use of equations (3) and (4). Equation (3) expresses a relationship between x-y coordinates at the point (x, y) and the angle $\phi$. Equation (4) defines a tangent of the Bragg angle $\theta_0$ of the mirror as "a". Equation (5), which is a differential equation, is solved to obtain equation (6), which is transformed to equation (7).

Figure 4:
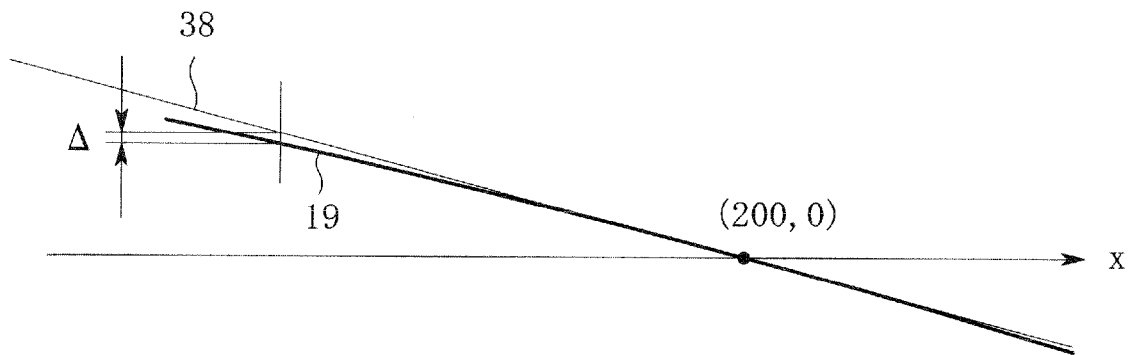
FIG. 4 shows an explanatory illustration of a shape of the reflective surface of the mirror and shows concerned mathematical equations.

A relationship shown in equation (8) in FIG. 4 is applied to equation (7) in FIG. 3, and the resultant equation is transformed to obtain equation (9) in FIG. 4. Equation (9) expresses the x-coordinate of any point (x, y) on the reflective surface 19. Thus, x-coordinate can be calculated with the use of the distance r, the angle $\phi$, and the Bragg angle $\theta_0$. A combination of equations (9) and (3) brings equation (10), which gives y-coordinate. A combination of equations (9) and (10) defines the shape of the reflective surface 19 of the mirror.

Referring to FIG. 4, how much the reflective surface of the mirror 19 is curved will be calculated below. Assuming that r is 200 millimeters, a distance $\Delta$ in y-direction between the tangential line 38 (which is a straight line) of the reflective surface 19 at the center (200, 0) of the reflective surface 19 and the reflective surface 19 (which is a curved line) can be calculated as described below. An equation of the tangential line 38 is expressed by equation (11) in FIG. 4. Y-coordinate on the tangential line is defined as $y_{tan}$. On the other hand, y-coordinate of the reflective surface 19 is expressed by equation (10). Table 1 shown below indicates the above-described distances $\Delta$, which are calculated with the use of the angle $\phi$ as a parameter. For example, when $\phi$ is two degrees, x-coordinate on the reflective surface 19 is 173.099 millimeters and y-coordinate is 6.045 millimeters. Y-coordinate on the tangential line 38 at the same x-coordinate, i.e., $y_{tan}$, is 6.528 millimeters. Accordingly, subtracting y-coordinate of the reflective surface 19 from y-coordinate of the tangential line 38 brings 0.483 millimeter, which is the distance $\Delta$. Similarly, there are also shown in the table the $\Delta$ values for $\phi$ being one degree, zero degree, negative one degree, and negative two degrees. Since y-coordinate of the reflective surface 19 is always less than y-coordinate of the tangential line when $\phi$ is increased and also decreased from zero degree, it is understood that the reflective surface 19 is slightly curved to be concave downward.

TABLE 1

| | $\phi$ (°) | | | | |
|---|---|---|---|---|---|
| | 2 | 1 | 0 | −1 | −2 |
| x (mm) | 173.099 | 186.092 | 200 | 214.882 | 230.801 |
| y (mm) | 6.045 | 3.248 | 0 | −3.751 | −8.060 |
| $y_{tan}$ (mm) | 6.528 | 3.375 | 0 | −3.611 | −7.474 |
| $\Delta$ (mm) | 0.483 | 0.127 | 0 | 0.140 | 0.586 |

Figure 5:
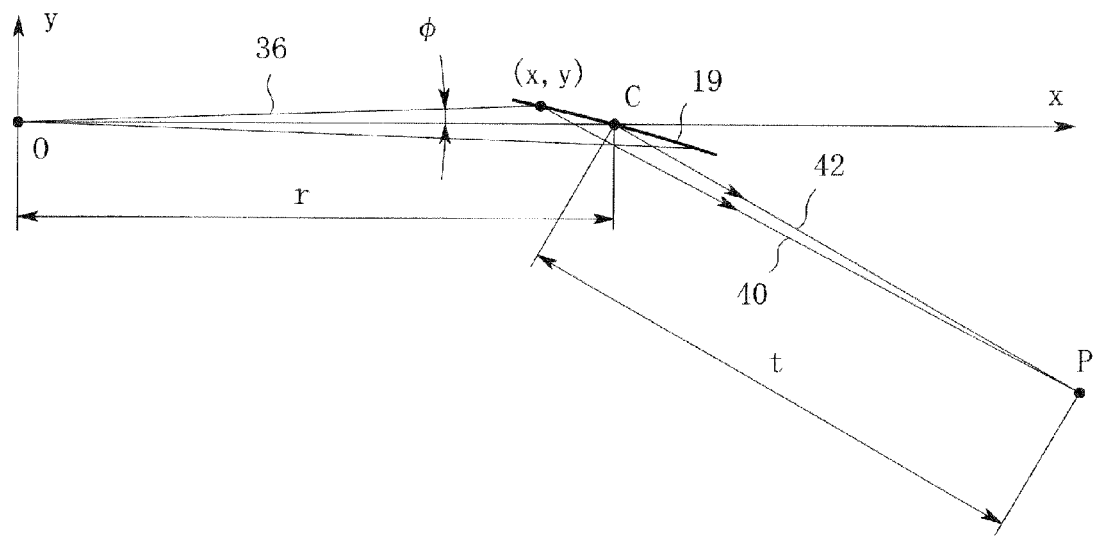
FIG. 5 shows an explanatory illustration indicating tracks of X-rays after reflected at the mirror and shows concerned mathematical equations.

Next, the track of an X-ray that has been reflected at the reflective surface will be described below. Referring to FIG. 5, the diffracted X-ray 36 that travels from the point O in a direction at the angle $\phi$ is reflected at the point (x, y) on the reflective surface 19 to become a reflected X-ray 40. On the other hand, the diffracted X-ray that travels from the point O along the x-axis is reflected at a point C on the reflective surface 19, the point C being an intersecting point of the reflective surface 19 and the x-axis, to become a reflected X-ray 42. The reflected X-ray 42 that has been reflected at the point C is to be called a central beam 42. A reflected X-ray 40 that has been reflected at any point (x, y) corresponding to the angle $\phi$ will intersect with the central beam 42 before long. The intersecting point is defined as a point P. A distance between the point C and the point P is defined as t.

Referring to FIG. 5, an equation of the reflected X-ray 40 that has been reflected at any point (x, y) corresponding to the angle $\phi$ is expressed by equation (13). Symbol A in equation (13) is defined by equation (12). An equation of the central beam 42 is expressed by equation (14). An intersecting point P has coordinates that satisfy both equations (13) and (14) at once, and therefore x-coordinate that satisfies the both equations gives x-coordinate of the point P, i.e., $x_p$, which is expressed by equation (15). Y-coordinate of the point P, i.e., $y_p$, may be calculated, for example, by applying the obtained $x_p$ to equation (14).

Table 2 shown below indicates coordinates ($x_p$, $y_p$) of the point P and distances t, which are calculated with the use of the angle $\phi$ as a parameter, under the condition that r is 200 millimeters and $\theta_0$ is 13.64 degrees. It is understood, according to the table 2, that each reflected X-ray intersects with the central beam at a place approximately 200 millimeters away from the center (point C) of the reflective surface of the mirror. Accordingly, in order to distinctly detect different reflected X-rays that have been reflected at different points on the reflective surface with the position sensitive X-ray detector, it is required to place the position sensitive X-ray detector somewhere between the point C and the point P. In this embodiment, it is preferable to place the position sensitive X-ray detector at a place approximately 50 to 100 millimeters away from the point C.

TABLE 2

| | $\phi$ (°) | | | | |
|---|---|---|---|---|---|
| | 2 | 1 | 0.5 | 0.1 | 0.01 |
| $x_p$ (mm) | 353.37 | 365.27 | 371.44 | 376.48 | 377.63 |
| $y_p$ (mm) | −79.09 | −85.23 | −88.41 | −91.01 | −91.60 |
| t (mm) | 172.56 | 185.95 | 192.89 | 198.56 | 199.86 |
| | $\phi$ (°) | | | | |
| | −0.01 | −0.1 | −0.5 | −1 | −2 |
| $x_p$ (mm) | 377.88 | 379.04 | 384.23 | 390.85 | 404.60 |
| $y_p$ (mm) | −91.73 | −92.33 | −95.01 | −98.42 | −105.51 |
| t (mm) | 200.14 | 201.45 | 207.29 | 214.73 | 230.20 |

Next, an angular separation function of the position sensitive X-ray detector will be described below. Referring to FIG. 6, the detector plane of the position sensitive X-ray detector 20 is placed away from the center (point C) of the reflective surface 19 of the mirror by a distance d. The detector plane is arranged nearly perpendicular to the central beam 42. The reflected X-ray 40 from the point (x, y) having the angle $\phi$ reaches a point Q on the detector plane. The central beam 42 from the point C reaches a point M on the detector plane. The distance between the point Q and the point M is s. Different reflected X-rays coming from plural different points on the reflective surface of the mirror are to reach plural different points on the X-ray detector respectively.

The coordinates ($x_m$, $y_m$) of the point M is expressed by equation (16) in FIG. 6. An equation of a straight line 44 that represents the detector plane is expressed by equation (17). The point Q is an intersecting point of the straight line 44 with the reflected X-ray 40. Since the straight line 44 is expressed by equation (17) in FIG. 6 whereas the reflected X-ray 40 is expressed by equation (13) in FIG. 5, the coordinates $(x_q, y_q)$ of the point Q may be obtained by solving the two equations, leading to equations (18) and (19). The distance s between the points Q and M may be calculated with the use of equation (16) expressing the coordinates of the point M and equations (18) and (19) both expressing the coordinates of the point Q, leading to equation (20).

Table 3 shown below indicates distances s on the detector plane, which are calculated with the use of the angle $\phi$ as a parameter, under the condition that r is 200 millimeters, $\theta_0$ is 13.64 degrees, and d is 50 millimeters. When $\phi$ is two degrees, the point Q is 4.28 millimeters away from the point M, whereas when $\phi$ is negative two degrees, the point Q is 6.29 millimeters away from the point M in the opposite direction. Accordingly, assuming that the diffracted X-rays are captured by the mirror within a range between positive and negative two degrees in $2\theta$, i.e., within a range between positive and negative two degrees in $\phi$, the lateral size of the detector must be at least about ten millimeters when the detector is placed at a point of 50 millimeters in distance d. If the region of ten millimeters is divided into a hundred channels for example, i.e., 0.1 millimeter per one channel, the diffracted X-ray is to be detected with a positional resolution of about 0.04 degree in a range of four degrees in $2\theta$. It is noted that since a variation of the angle $\phi$ (i.e., variation of $2\theta$) is not proportional to a variation of s on the detector plane, a characteristic curve of a variation of s to a variation of $\phi$ should be prepared based on equation (20) in FIG. 6, so that it is determined what channel of the detector receives what angle range in $\phi$ of an X-ray.

TABLE 3

| | $\phi$ (°) | | | | |
|---|---|---|---|---|---|
| | 2 | 1 | 0.5 | 0.1 | 0.05 |
| s (mm) | 4.28 | 2.37 | 1.25 | 0.259 | 0.130 |
| | $\phi$ (°) | | | | |
| | 0.04 | 0.03 | 0.02 | 0.01 | |
| s (mm) | 0.104 | 0.078 | 0.052 | 0.026 | |
| | $\phi$ (°) | | | | |
| | −0.01 | −0.02 | −0.03 | −0.04 | −0.05 |
| s (mm) | 0.026 | 0.053 | 0.079 | 0.105 | 0.132 |
| | $\phi$ (°) | | | | |
| | −0.1 | −0.5 | −1 | −2 | |
| s (mm) | 0.264 | 1.37 | 2.88 | 6.29 | |

As seen from FIG. 6, according to the present invention, plural different diffracted X-rays having different diffraction angles can be detected distinctly and simultaneously via the mirror with keeping the one-dimensional position sensitive X-ray detector 20 stationary. Thus, since different diffracted X-rays having different diffraction angles can be detected simultaneously, an X-ray detection intensity can be increased as compared to the case that only a diffracted X-ray having a single diffraction angle is detected at once with the use of the conventional analyzer crystal. Therefore, the present invention enables comparatively short-time diffraction pattern measurement even using the analyzer crystal. It is noted however that when the X-ray detector is kept stationary during measurement, a coverage angle is limited to a range of about four degrees in $2\theta$ for example. Therefore, in order to obtain the powder diffraction pattern over a wider angular range, the receiving optical system 30 should be rotated as shown in FIG. 2.

Figure 9:
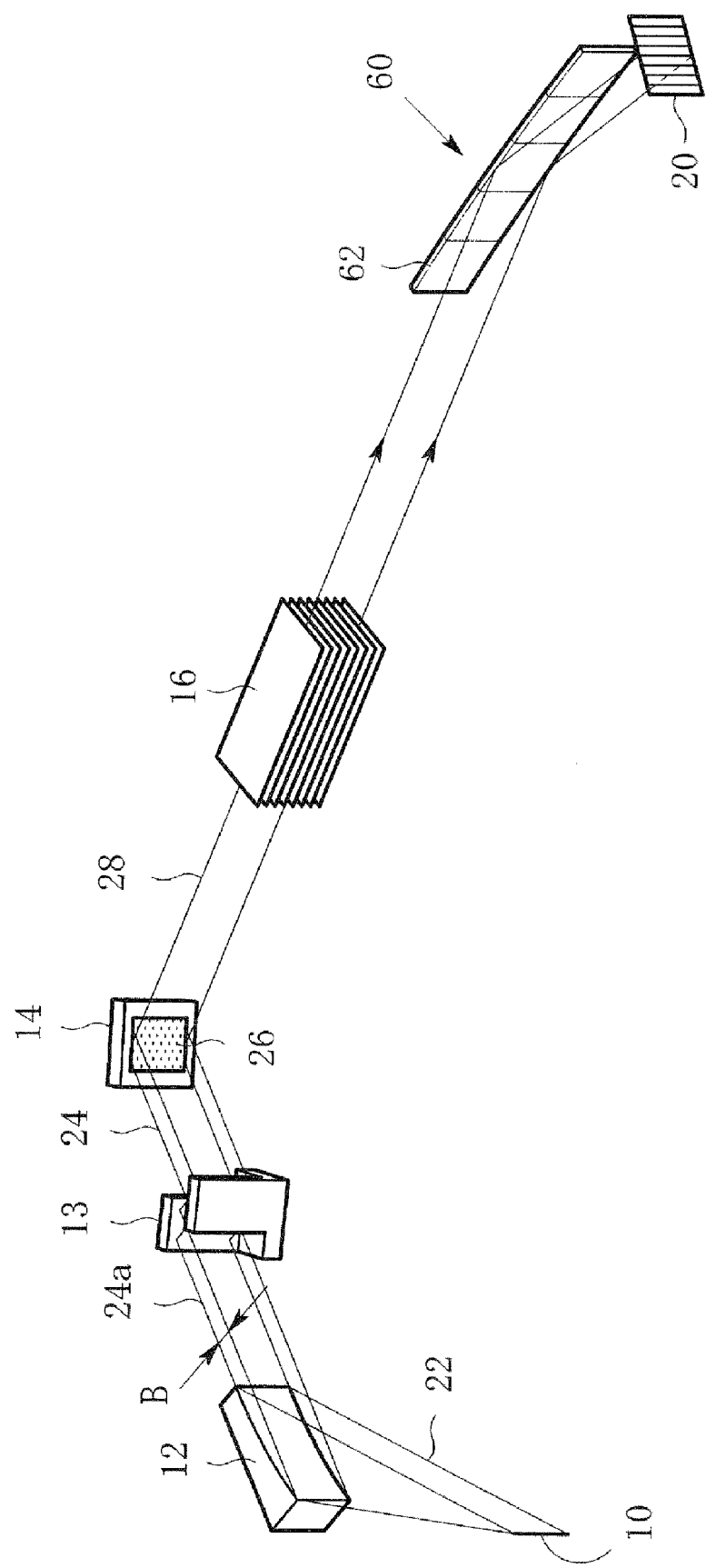
FIG. 9 is a schematic perspective view of an X-ray diffraction apparatus according to the second type of the present invention.
Figure 10:
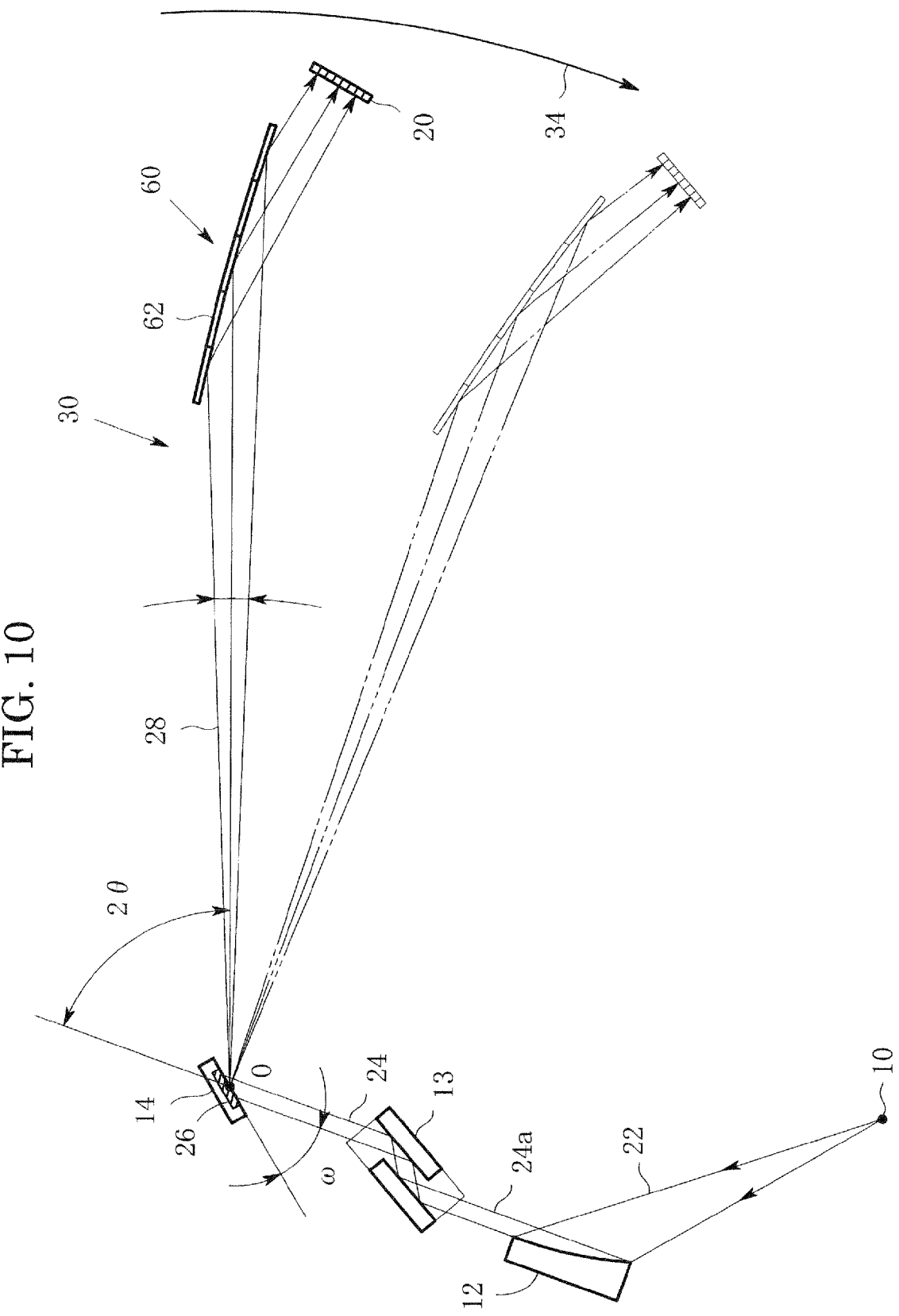
FIG. 10 is a plan view of the X-ray diffraction apparatus shown in FIG. 9.

Next, an X-ray diffraction apparatus according to the second type of the present invention will be described. FIG. 9 is a schematic perspective view of an X-ray diffraction apparatus according to the second type of the present invention. The X-ray diffraction apparatus of the second type shown in FIG. 9 is different in shape of the mirror 60 from the X-ray diffraction apparatus of the first type shown in FIG. 1. The configuration of the second type except for the mirror is the same as the first type shown in FIG. 1. FIG. 10 is a plan view of the X-ray diffraction apparatus shown in FIG. 9.

The shape of the reflective surface of the mirror 60 will be described in detail below. The mirror 60 is configured to combine plural flat reflective surfaces 62. In this embodiment, a partial mirror that constitutes each flat reflective surface 62 is made of a single crystal of Ge, and it is formed so that Ge(111) plane is parallel to the flat reflective surface 62 of the partial mirror. Each of the partial mirrors is to reflect, with the diffraction phenomena, the diffracted X-ray coming from the sample. The Ge(111) plane corresponds to the crystal lattice plane that causes diffraction.

The plural flat reflective surfaces 62 are an improvement of one curved reflective surface. The based curved reflective surface is shaped in an equiangular spiral in a plane parallel to the diffraction plane, the shape having been explained with reference to the above-mentioned FIGS. 3 and 4.

Figure 11:
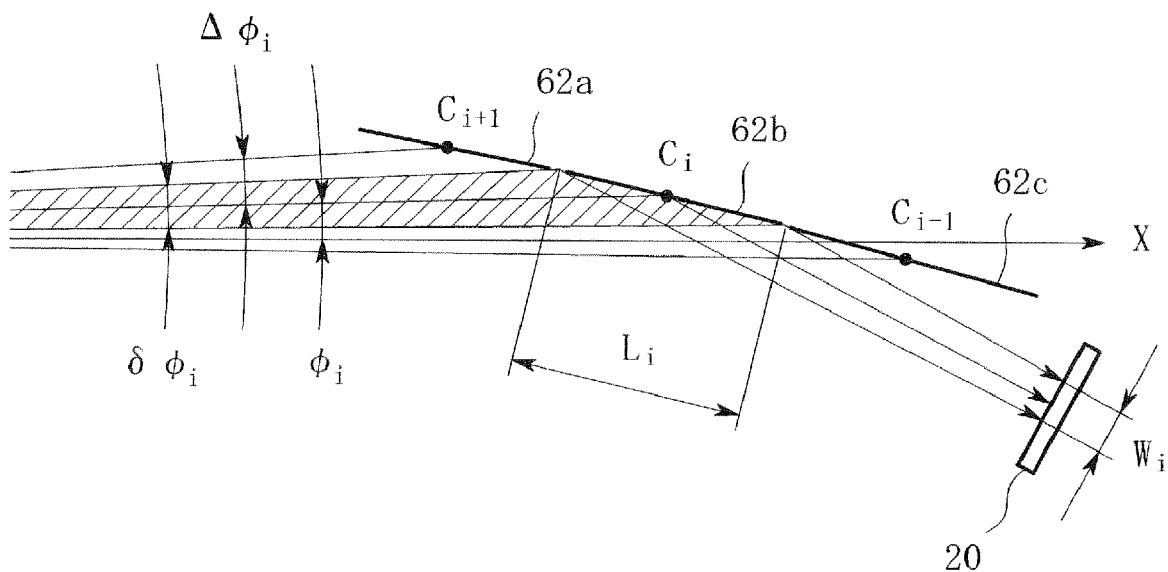
FIG. 11 shows an explanatory illustration of a mirror consisting of plural flat reflective surfaces and shows concerned mathematical equations.

Next, there will be described the procedure for making the plural flat reflective surfaces by dividing one curved reflective surface. FIG. 11 shows only three flat reflective surfaces 62a, 62b and 62c of the mirror that consists of a combination of plural flat reflective surfaces 62. The centers of all the flat reflective surfaces are located on the above-described equiangular spiral. A tangential line of the equiangular spiral at an assumed center of each flat reflective surface becomes the flat reflective surface itself. Taking an i-th flat reflective surface 62b for example, the center (point $C_i$) of the flat reflective surface 62b is at an angle $\phi_i$ to the x-axis. The length of the flat reflective surface 62b is $L_i$. An angular range of the diffracted X-ray captured by the flat reflective surface 62b is $\delta\phi_i$. An angle between a diffracted X-ray travelling toward the center (point $C_i$) of the flat reflective surface 62b and a diffracted X-ray travelling toward the center (point $C_{i+1}$) of the adjacent flat reflective surface 62a is $\Delta\phi_i$. A detection width with which the reflected X-ray that has been reflected at the flat reflective surface 62b impinges on the detector plane of the X-ray detector 20 is $W_i$.

A straight line equation of the i-th flat reflective surface 62b is expressed by equation (21) in FIG. 11. A symbol $A_i$ is defined by equation (22).

A method for dividing the equiangular spiral may use various setting conditions. Table 4 shown below indicates three conditions. The first condition is that the capture angular ranges $\delta\phi$ of the respective flat reflective surfaces are equal to one another. In this case, the mirror lengths L are different from one another, and also the detection widths W assigned to the respective flat reflective surfaces are different from one another. The second condition is that the mirror lengths L of the respective flat reflective surfaces are equal to one another. In this case, the capture angular ranges $\delta\phi$ of the respective flat reflective surfaces are different from one another, and also the detection widths W assigned to the respective flat reflective surfaces are different from one another. The third condition is that the detection widths W assigned to the respective flat reflective surfaces are equal to one another. In this case, the capture angular ranges δφ of the respective flat reflective surfaces are different from one another, and also the mirror lengths L are different from one another.

TABLE 4

|  | Angular range | Mirror length | Detection width |
|---|---|---|---|
| First condition | $δφ_1 = δφ_2 = \ldots = δφ_N = δφ$ | $L_1 > L_2 > \ldots > L_N$ | $W_1 > W_2 > \ldots > W_N$ |
| Second condition | $δφ_1 < δφ_2 < \ldots < δφ_N$ | $L_1 = L_2 = \ldots = L_N = L$ | $W_1 > W_2 > \ldots > W_N$ |
| Third condition | $δφ_1 < δφ_2 < \ldots < δφ_N$ | $L_1 < L_2 < \ldots < L_N$ | $W_1 = W_2 = \ldots = W_N = W$ |

Table 5 shown below Indicates a numerical example of the mirror consisting of a combination of eleven flat reflective surfaces under the above-described third condition, in which the detection widths W on the detector plane are equal to one another. These calculated values are based on the condition that the size of one channel of the X-ray detector is 0.1 millimeter and the detector has 128 channels. The table indicates that the detection width W (s in Table 5) corresponding to one flat reflective surface is 1.1636 millimeters. An actual device based on the numerical example will be described below. Assuming that W is 1.1 millimeters, the width of one channel of the X-ray detector is 0.1 millimeter, and the detector has 121 channels, one channel-group consisting of eleven channels is to be assigned to one flat reflective surface. The reflected X-ray that has been reflected at the center of each flat reflective surface reaches the point Q (see FIG. 6) on the detector plane, the coordinates of the point Q being ($x_p$, $y_p$). An angle (to the x-axis) of the diffracted X-ray travelling toward the center of each flat reflective surface is φ. A distance between the point Q and the center M of the detector plane is s (see FIG. 6). The numerical values in FIG. 5 are calculated under the condition that r is 200 millimeters, $θ_0$ is 13.64 degrees, and d is 50 millimeters.

TABLE 5

| Number | s(mm) | $x_q$(mm) | $y_q$(mm) | φ(°) |
|---|---|---|---|---|
| 1 | −5.8182 | 247.1055 | −17.7459 | −1.8705 |
| 2 | −4.6545 | 246.5722 | −18.7801 | −1.5411 |
| 3 | −3.4909 | 246.0389 | −19.8144 | −1.1928 |
| 4 | −2.3273 | 245.5055 | −20.8486 | −0.8227 |
| 5 | −1.1636 | 244.9722 | −21.8828 | −0.4268 |
| 6 | 0.0000 | 244.4388 | −22.9170 | 0.0000 |
| 7 | 1.1636 | 243.9055 | −23.9512 | 0.4650 |
| 8 | 2.3273 | 243.3722 | −24.9854 | 0.9786 |
| 9 | 3.4909 | 242.8388 | −26.0196 | 1.5572 |
| 10 | 4.6545 | 242.3055 | −27.0539 | 2.2291 |
| 11 | 5.8182 | 241.7721 | −28.0881 | 3.0516 |

Table 6 shown below indicates a numerical example of the flat reflective surfaces when the mirror consists of a combination of eleven flat reflective surfaces under the condition shown in the above-described FIG. 5. An angle φ is an angle at the center of each flat reflective surface. The coordinates (x, y) are shown for the center and the both ends of each flat reflective surface. For example, as to the first flat reflective surface, x-coordinate of the center is 228.6781 millimeters and its y-coordinate is negative 7.4681 millimeters, x-coordinate of one end is 231.3450 millimeters and its y-coordinate is negative 8.2081 millimeters, and x-coordinate of the other end is 226.0113 millimeters and its y-coordinate is negative 6.7281 millimeters. The symbol L represents a length of each flat reflective surface. The symbol Δφ represents an angle between the centers of two adjacent flat reflective surfaces. The total length of the eleven flat reflective surfaces is about 80 millimeters.

TABLE 6

| Number | φ (°) | Δφ (°) | x (mm) | y (mm) | L (mm) |
|---|---|---|---|---|---|
|  |  |  | 231.3450 | −8.2081 |  |
| 1 | −1.8705 |  | 228.6781 | −7.4681 | 5.5352 |
|  |  | 0.3294 | 226.0113 | −6.7281 |  |
| 2 | −1.5411 |  | 223.3621 | −6.0091 | 5.6007 |
|  |  | 0.3483 | 220.6060 | −5.2614 |  |
| 3 | −1.1928 |  | 217.8684 | −4.5363 | 5.7905 |
|  |  | 0.3701 | 215.0085 | −3.7789 |  |
| 4 | −0.8227 |  | 212.1693 | −3.0467 | 6.0108 |
|  |  | 0.3959 | 209.1881 | −2.2778 |  |
| 5 | −0.4268 |  | 206.2291 | −1.5363 | 6.2748 |
|  |  | 0.4268 | 203.1015 | −0.7526 |  |
| 6 | 0.0000 |  | 200.0000 | 0.0000 | 6.5945 |
|  |  | 0.4650 | 196.6929 | 0.8026 |  |
| 7 | 0.4650 |  | 193.4158 | 1.5696 | 6.9972 |
|  |  | 0.5136 | 189.8799 | 2.3974 |  |
| 8 | 0.9786 |  | 186.3800 | 3.1836 | 7.5238 |
|  |  | 0.5786 | 182.5391 | 4.0466 |  |
| 9 | 1.5572 |  | 178.7427 | 4.8592 | 8.2571 |
|  |  | 0.6719 | 174.4649 | 5.7750 |  |
| 10 | 2.2291 |  | 170.2446 | 6.6267 | 9.3902 |
|  |  | 0.8225 | 165.2603 | 7.6327 |  |
| 11 | 3.0516 |  | 160.3596 | 8.5488 | 9.9712 |
|  |  |  | 155.4589 | 9.4649 |  |
| Total |  |  |  |  | 77.9460 |

The mirror consisting of a combination of plural flat reflective surfaces has an advantage described below as compared to the curved mirror shaped in an equiangular spiral. When using the curved mirror, one channel may receive, in principle, not only a diffracted X-ray having the intended angle 2θ but also other diffracted X-rays having other angles within a small angular range unless the channel width of the detector is infinitely narrowed. In contrast, when using the mirror consisting of a combination of plural flat reflective surfaces, a certain channel group assigned to a certain flat reflective surface is to receive diffracted X-rays having the same diffraction angles, so that the resultant angular resolution is increased up to the angular resolution of the analyzer crystal.

Figure 12:
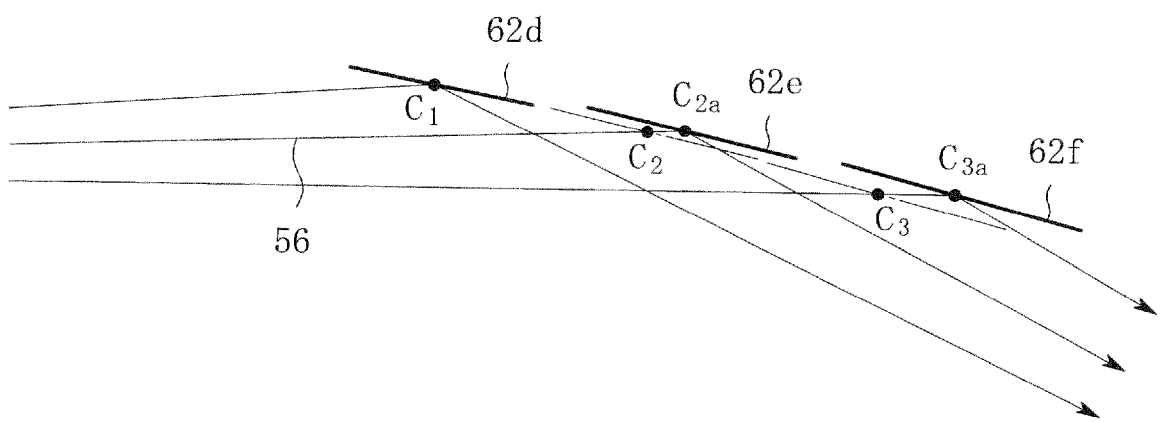
FIG. 12 shows a modification in which the centers of the flat reflective surfaces are shifted from an equiangular spiral.

FIG. 12 shows a modification in which the coordinates of the centers of the respective flat reflective surfaces are shifted from an equiangular spiral. It is assumed, for example, that the centers $C_1$, $C_2$ and $C_3$ of three flat reflective surfaces 62d, 62e and 62f are located on one equiangular spiral. When the central flat reflective surface 62e is slightly translated in the travelling direction of a diffracted X-ray 56, the flat reflective surface 62e is moved with keeping its slope so that its center $C_2$ is moved to $C_{2a}$. Even with the translation, an angle of the flat reflective surface 62e to the diffracted X-ray 56 is kept as it is, and therefore the diffracted X-ray 56 is reflected at the flat reflective surface 62e. The right-side flat reflective surface 62f is similarly translated so that the center $C_3$ is moved to $C_{3a}$, noting that its translational distance is larger than that for the central flat reflective surface 62e. Even if the plural flat reflective surfaces are shifted sequentially as mentioned above, the resultant combination mirror can properly reflect the diffracted X-rays, noting however that detection points of the reflected X-rays on the detector plane are also shifted along with the shift of the flat reflective surfaces. Accordingly, if using a large detection plane, the modification shown in FIG. 12 is preferable.

Figure 13:
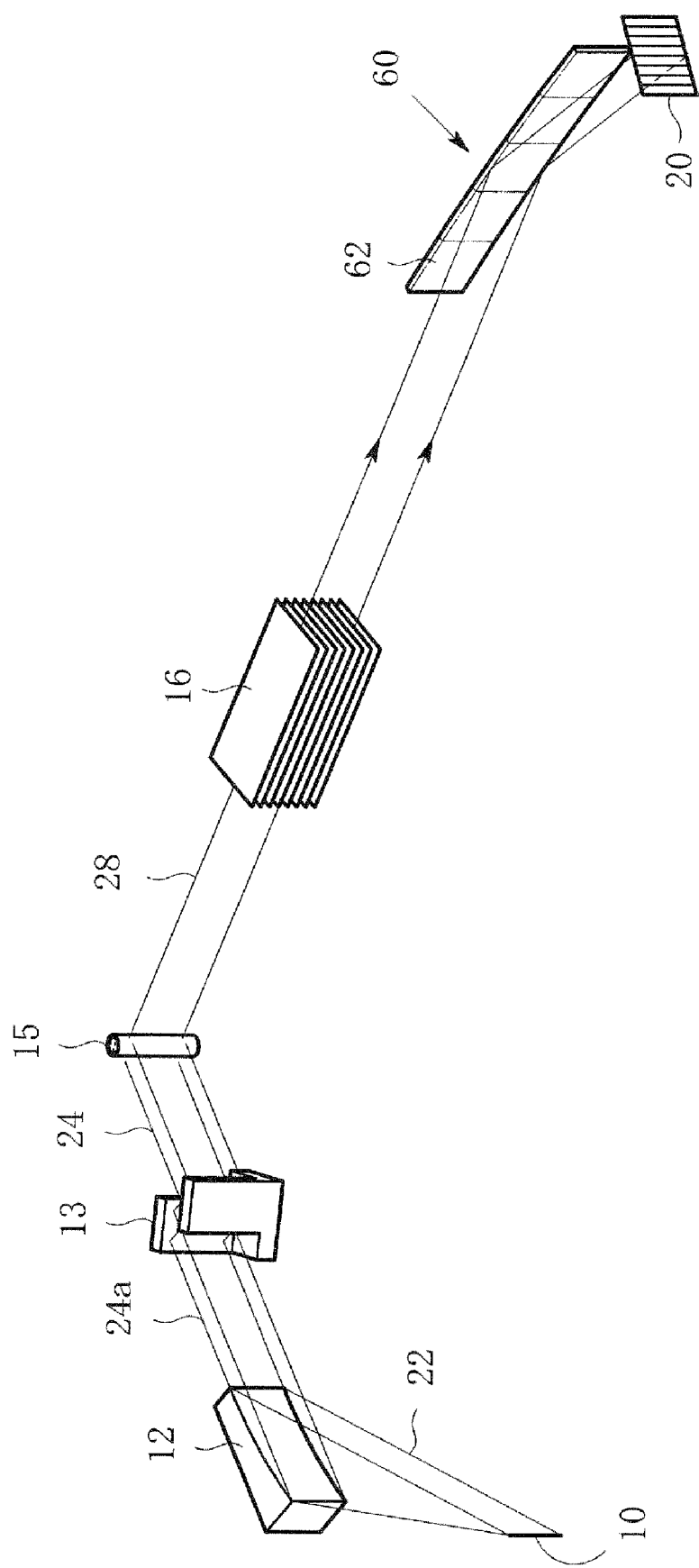
FIG. 13 is a schematic perspective view of a modified optical system of the X-ray diffraction apparatus shown in FIG. 9.

FIG. 13 shows a modification using a sample holder for transmission-type X-ray diffraction analysis in the X-ray diffraction apparatus, shown in FIG. 9, according to the second type of the present invention as well as the modification shown in FIG. 7. For example, a capillary tube 15 may be filled with a sample.

Figure 14:
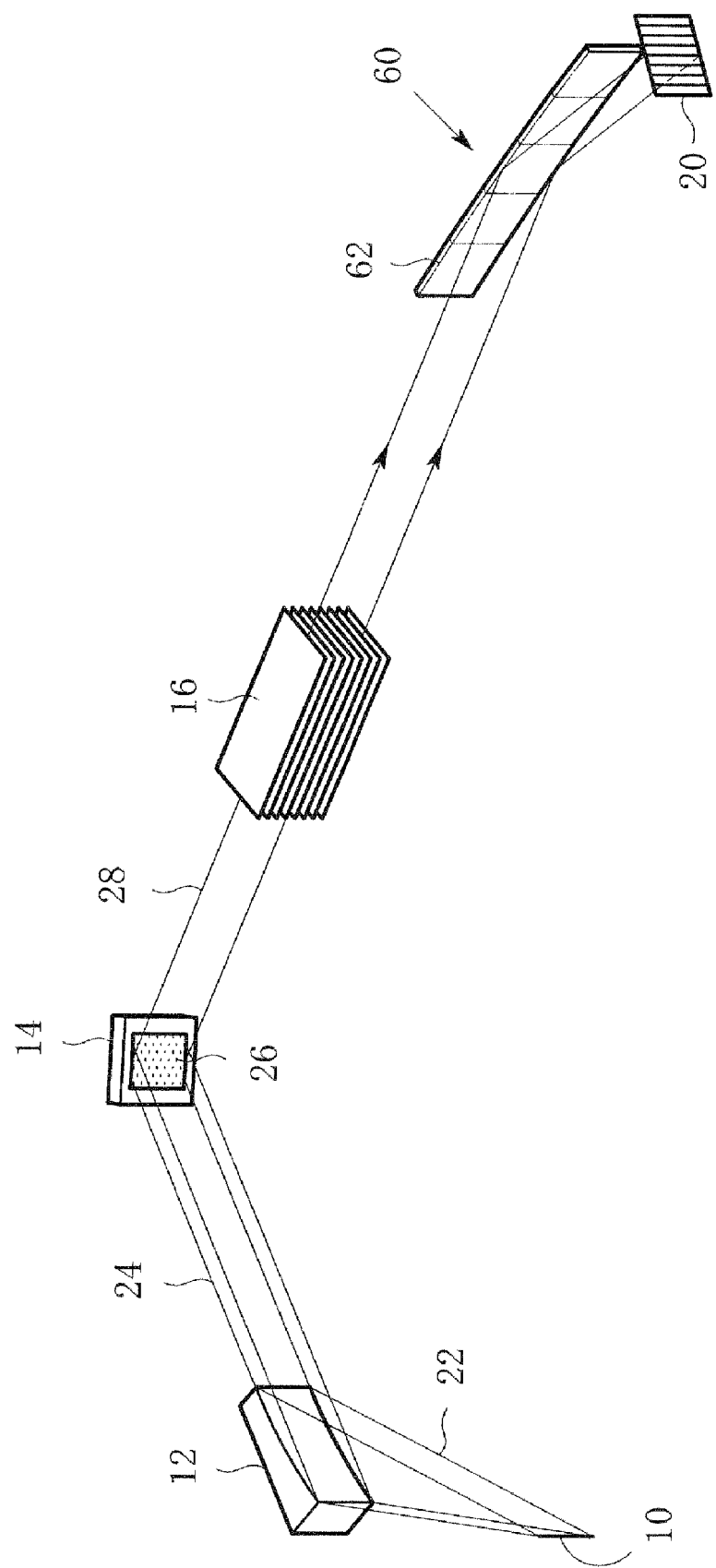
FIG. 14 is a schematic perspective view of another modified optical system of the X-ray diffraction apparatus shown in FIG. 9.

FIG. 14 shows a modified optical system of the X-ray diffraction apparatus, shown in FIG. 9, according to the second type of the present invention as well as the modification shown in FIG. 8. The modified embodiment differs from the apparatus shown in FIG. 9 in that the channel cut monochromator is omitted in the incident-side optical system, and the multilayer mirror 12 is optimized for the X-ray wavelength to be used in this embodiment (CuKα in this embodiment, i.e., the doublet of CuKα1 and CuKα2).

Although the above description mentions the case that the X-ray focus is the linear focus, the present invention may be applied to the point focus.

What is claimed is:

1. An X-ray diffraction apparatus comprising:
a device for generating an X-ray parallel beam to be made incident on a sample;
a mirror for reflecting diffracted X-rays from the sample, wherein the mirror utilizes a diffraction phenomena and has a reflective surface which is formed so that: (i) an angle that is defined in a plane parallel to a diffraction plane becomes constant, wherein the angle is between a tangential line of the reflective surface at any point on the reflective surface and a line segment connecting said any point on the reflective surface and the sample, and (ii) a crystal lattice plane that causes reflection is parallel to the reflective surface at any point on the reflective surface; and
an X-ray detector for detecting the reflected X-rays from the mirror, wherein the X-ray detector is one-dimensional position sensitive in a plane parallel to the diffraction plane;
wherein a relative positional relationship between the mirror and the X-ray detector is determined, in the plane parallel to the diffraction plane, so that the reflected X-rays from different points on the reflective surface of the mirror reach different points on the X-ray detector respectively.

2. The X-ray diffraction apparatus according to claim 1, wherein the reflective surface of the mirror is shaped in an equiangular spiral in the plane parallel to the diffraction plane, a center of the equiangular spiral being located on a surface of the sample.

3. An X-ray diffraction method for an X-ray diffraction apparatus including: (i) a device for generating an X-ray parallel beam to be made incident on a sample; (ii) a mirror for reflecting diffracted X-rays from the sample, wherein the mirror utilizes a diffraction phenomena and has a reflective surface which is formed so that: (a) an angle that is defined in a plane parallel to a diffraction plane becomes constant, wherein the angle is between a tangential line of the reflective surface at any point on the reflective surface and a line segment connecting said any point on the reflective surface and the sample, and (b) a crystal lattice plane that causes reflection is parallel to the reflective surface at any point on the reflective surface; and (iii) an X-ray detector for detecting the reflected X-rays from the mirror, wherein the X-ray detector is one-dimensional position sensitive in a plane parallel to the diffraction plane; said X-ray diffraction method comprising:
determining a relative positional relationship between the mirror and the X-ray detector, in the plane parallel to the diffraction plane, so that the reflected X-rays from different points on the reflective surface of the mirror reach different points on the X-ray detector respectively;
allowing the X-ray parallel beam to be incident on the sample; and
detecting different diffracted X-rays, which have been reflected at the mirror and have different diffraction angles, distinctly and simultaneously.

4. The X-ray diffraction method according to claim 3, wherein the reflective surface of the mirror is shaped in an equiangular spiral in the plane parallel to the diffraction plane, a center of the equiangular spiral being located on a surface of the sample.

5. An X-ray diffraction apparatus comprising:
a device for generating an X-ray parallel beam to be made incident on a sample;
a mirror for reflecting diffracted X-rays from the sample, wherein the mirror utilizes diffraction phenomena and has a reflective surface comprising a combination of plural flat reflective surfaces which are located so that: (i) an angle that is defined in a plane parallel to a diffraction plane becomes constant among the plural flat reflective surfaces, wherein the angle is between each flat reflective surface and a line segment connecting a center of each respective flat reflective surface and the sample, and (ii) a crystal lattice plane that causes reflection is parallel to each respective flat reflective surface; and
an X-ray detector for detecting the reflected X-rays from the mirror, wherein the X-ray detector is one-dimensional position sensitive in a plane parallel to the diffraction plane;
wherein a relative positional relationship between the flat reflective surfaces and the X-ray detector is determined, in the plane parallel to the diffraction plane, so that the reflected X-rays that have been reflected at different flat reflective surfaces reach different points on the X-ray detector respectively.

6. The X-ray diffraction apparatus according to claim 5, wherein the respective centers of the flat reflective surfaces are located, in the plane parallel to the diffraction plane, on an equiangular spiral having a center that is located on a surface of the sample.

7. The X-ray diffraction apparatus according to claim 5, wherein a center of at least one of the flat reflective surfaces is shifted, in the plane parallel to the diffraction plane, from a point on an equiangular spiral having a center that is located on a surface of the sample.

8. The X-ray diffraction apparatus according to claim 5, wherein capture angular ranges of the respective flat reflective surfaces are equal to one another.

9. The X-ray diffraction apparatus according to claim 5, wherein mirror lengths L of the respective flat reflective surfaces are equal to one another.

10. The X-ray diffraction apparatus according to claim 5, wherein detection widths W assigned to the respective flat reflective surfaces are equal to one another.

11. An X-ray diffraction method for an X-ray diffraction apparatus including: (i) a device for generating an X-ray parallel beam which can be made incident on a sample; (ii) a mirror for reflecting diffracted X-rays from the sample, wherein the mirror utilizes diffraction phenomena and has a reflective surface comprising a combination of plural flat reflective surfaces which are located so that: (a) an angle that is defined in a plane parallel to a diffraction plane becomes constant among the plural flat reflective surfaces, wherein the angle is between each flat reflective surface and a line segment connecting a center of each respective flat reflective surface and the sample, and (b) a crystal lattice plane that causes reflection is parallel to each respective flat reflective surface; and (iii) an X-ray detector for detecting the reflected X-rays from the mirror, wherein the X-ray detector is one-dimensional position sensitive in a plane parallel to the diffraction plane; said X-ray diffraction method comprising:

determining a relative positional relationship between the flat reflective surfaces and the X-ray detector, in the plane parallel to the diffraction plane, so that the reflected X-rays that have been reflected at different flat reflective surfaces reach different points on the X-ray detector respectively;

allowing the X-ray parallel beam to be incident on the sample; and detecting different diffracted X-rays, which have been reflected at the mirror and have different diffraction angles, distinctly and simultaneously.

12. The X-ray diffraction method according to claim 11, wherein the respective centers of the flat reflective surfaces are located, in the plane parallel to the diffraction plane, on an equiangular spiral having a center that is located on a surface of the sample.

13. The X-ray diffraction method according to claim 11, wherein a center of at least one of the flat reflective surfaces is shifted, in the plane parallel to the diffraction plane, from a point on an equiangular spiral having a center that is located on a surface of the sample.

\* \* \* \* \*